US011311529B2

(12) United States Patent
Jindal et al.

(10) Patent No.: US 11,311,529 B2
(45) Date of Patent: *Apr. 26, 2022

(54) TOPICAL FORMULATIONS OF 5-α-REDUCTASE INHIBITORS AND USES THEREOF

(71) Applicant: Varsona Therapeutics, Inc., San Francisco, CA (US)

(72) Inventors: Vinay K. Jindal, San Francisco, CA (US); Manu Gujrati, San Francisco, CA (US); Mary Angelica Oba Magsombol-Karaan, Rohnert Park, CA (US)

(73) Assignee: Varsona Therapeutics, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,657

(22) Filed: Nov. 7, 2019

(65) Prior Publication Data

US 2020/0147071 A1    May 14, 2020

Related U.S. Application Data

(60) Provisional application No. 62/889,318, filed on Aug. 20, 2019, provisional application No. 62/757,483, filed on Nov. 8, 2018.

(51) Int. Cl.
*A61K 31/473* (2006.01)
*A61P 17/14* (2006.01)
*A61K 9/00* (2006.01)
*A61K 47/10* (2017.01)
*A61K 47/44* (2017.01)

(52) U.S. Cl.
CPC .......... *A61K 31/473* (2013.01); *A61K 9/0014* (2013.01); *A61K 47/10* (2013.01); *A61K 47/44* (2013.01); *A61P 17/14* (2018.01)

(58) Field of Classification Search
None
See application file for complete search history.

(56) References Cited

U.S. PATENT DOCUMENTS

| | | | | |
|---|---|---|---|---|
| 4,339,276 A * | 7/1982 | Yokoyama | ............... | C08L 91/08 106/271 |
| 4,950,475 A * | 8/1990 | Vishnupad | ........... | A61K 8/0208 261/DIG. 88 |
| 5,030,374 A * | 7/1991 | Tranner | .................... | A61K 8/39 510/137 |
| 5,422,361 A * | 6/1995 | Munayyer | ............ | A61K 9/0014 514/396 |
| 5,914,334 A * | 6/1999 | Charu | .................. | A61K 9/0014 514/337 |
| 7,854,940 B2 * | 12/2010 | Ciccognani | ............ | A01N 31/14 424/404 |
| 10,441,567 B2 | 10/2019 | Zhi | | |
| 2002/0035070 A1 | 3/2002 | Gardlik et al. | | |
| 2003/0191035 A1 | 10/2003 | Verboom et al. | | |
| 2004/0167046 A1 | 8/2004 | Lukenbach et al. | | |
| 2006/0204588 A1 | 9/2006 | Liversidge et al. | | |
| 2007/0202180 A1 | 8/2007 | Liversidge et al. | | |
| 2008/0260864 A1 | 10/2008 | Dascalu | | |
| 2010/0048598 A1 | 2/2010 | Kandavilli et al. | | |
| 2011/0212167 A1 | 9/2011 | Ali et al. | | |
| 2014/0079686 A1 | 3/2014 | Barman et al. | | |
| 2014/0322148 A1 | 10/2014 | Jackson | | |
| 2015/0216986 A1 | 8/2015 | Pohlmann et al. | | |
| 2019/0022000 A1 | 1/2019 | Tamarkin et al. | | |
| 2019/0091149 A1 | 3/2019 | Tamarkin et al. | | |
| 2019/0224109 A1 | 7/2019 | Florence et al. | | |
| 2021/0353643 A1 | 11/2021 | Jindal et al. | | |

FOREIGN PATENT DOCUMENTS

| | | | |
|---|---|---|---|
| EP | 0027286 A2 * | 4/1981 | ............. A61K 8/602 |
| WO | WO-2018/013142 A1 | 1/2018 | |
| WO | WO 2019/012353 A1 | 1/2019 | |
| WO | WO-2021/231727 A1 | 11/2021 | |

OTHER PUBLICATIONS

Karatas et al. "Management of Hair Loss Associated with Endocrine Therapy in Patients with Breast Cancer: An Overview". SpringerPlus. 2016; 5:585. (Year: 2016).*
Lubrizol LifeSciences. "Promulgen D Nonionic Emulsifier". Technical Data Sheet. Published Nov. 5, 2014. pp. 1-2. (Year: 2014).*
The Concise Oxford Dictionary (Tenth Edition). Ed. J. Pearsall. "Emulsion". Oxford University Press. 1999. p. 468. (Year: 1999).*
Ali et al. "Preparation, Characterization and Stability Study of Dutasteride Loaded Nanoemulsion for Treatment of Benign Prostatic Hypertrophy". Iranian Journal of Pharmaceutical Research. 2014; 13(4):1125-1140. (Year: 2014).*
Rozner et al. "Safety of 5alpha-Reductase Inhibitors and Spironolactone in Breast Cancer Patients Receiving Endocrine Therapies". Breast Cancer Research and Treatment. 2019; 174:15-26, Published Online Nov. 22, 2018. (Year: 2018).*

(Continued)

*Primary Examiner* — Leslie A. Royds Draper
(74) *Attorney, Agent, or Firm* — Clark & Elbing LLP

(57) ABSTRACT

Disclosed herein are topical compositions of 5-α reductase inhibitors, such as dutasteride or finasteride, or a pharmaceutically acceptable salt, ester, or derivative thereof and the use of the compositions for the treatment of hair loss secondary to endocrine therapy in patients with breast cancer (Endocrine Therapy-Induced Alopecia or ETIA), androgenetic alopecia (AGA), alopecia areata, and hirsutism. The topical composition is advantageous over the existing oral compositions of 5-α reductase inhibitors because the topical composition is safer and more effective. The topical formulation may allow for a slow release of the active ingredient dutasteride, better penetration at the therapeutically effective amount of dutasteride with an improved safety profile because it does not need to travel through the bloodstream to be efficacious, thereby minimizing the risk of systemic side effects.

14 Claims, 2 Drawing Sheets

(56) References Cited

OTHER PUBLICATIONS

Bhatia, A., et al., "Tamoxifen-loaded liposomal topical formulation arrests hair growth in mice", British Journal of Dermatology, 2010, vol. 163, pp. 412-415.
Clark, R. V., et al., "Marked Suppression of Dihydrotestosterone in Men with Benign Prostatic Hyperplasia by Dutasteride, a Dual 5α-Reductase Inhibitor", J Clin Endocrinol Metab, 2004, vol. 89, No. 5, pp. 2179-2184.
Gallicchio, L, et al., "Aromatase inhibitor therapy and hair loss among breast cancer survivors", Breast Cancer Res Treat, 2013, vol. 142, pp. 435-443.
Herskovitz, I., et al., "Female Pattern Hair Loss", Int J Endocrinol Metab, 2013, vol. 11, No. 4, pp. 1-8.
Jain, R., et al., "Potential targets in the discovery of new hair growth promoters for androgenic alopecia", Expert Opin. Ther. Targets, 2014, vol. 18, No. 7, pp. 1-20.
Lindner, J., et al., "Hair shaft abnormalities after chemotherapy and tamoxifen therapy in patients with breast cancer evaluated by optical coherence tomography", British Journal of Dermatology, 2012, vol. 167, pp. 1272-1278.
Olsen, E. A., et al., "The importance of dual 5α-reductase inhibition in the treatment of male pattern hair loss: Results of a randomized placebo-controlled study of dutasteride versus finasteride", J Am Acad Dermatol, 2006, vol. 55, No. 6, pp. 1014-1023.
Saggar, V., et al., "Alopecia With Endocrine Therapies in Patients With Cancer", The Oncologist, 2013, vol. 18, pp. 1126-1134.
Sawaya, M. E., et al., "Different Levels of 5α-Reductase Type I and II, Aromatase, and Androgen Receptor in Hair Follicles of Women and Men with Androgenetic Alopecia", J Invest Dermatol, 1997, vol. 109, No. 3, pp. 296-300.
Shapiro, J., et al., "Hair Loss in Women", N Engl J Med, 2007, vol. 357, pp. 1620-1630.
Wang, J., et al., "Protection Against Chemotherapy-Induced Alopecia", Pharmaceutical Research, 2006, vol. 23, No. 11, pp. 2505-2514.
Farshi et al., "A randomized double blind, vehicle controlled bilateral comparison study of the efficacy and safety of finasteride 0.5% solution in combination with intense pulsed light in the treatment of facial hirsutism," J Cosmet Laser Ther. 14(4):193-9 (2012).
Frank, Chapter 136: Pituitary Pars Intermedia Dysfunction. *Robinson's Current Therapy in Equine Medicine*, Seventh Edition. Sprayberry and Robinson, Elsevier, 574 (2015).
Freites-Martinez et al., "Endocrine Therapy-Induced Alopecia in Patients With Breast Cancer," JAMA Dermatol. 154(6):670-5 (2018) (12 pages).
International Search Report and Written Opinion for International Application No. PCT/US19/60194, dated Jan. 13, 2020 (14 pages).
Rowland et al., "Androgenic alopecia: the risk-benefit ratio of Finasteride," J Mind Med Sci. 5(1):1-6 (2018) (8 pages).
FDA Label for Avodart (19 pages) (2008).
Rozner et al., "Safety of 5α-reductase inhibitors and spironolactone in breast cancer patients receiving endocrine therapies," Breast Cancer Res Treat. 174(1): 15-26 (2019).
Rugo et al., "Alopecia related to systemic cancer therapy," UpToDate. (26 pages) (2020).
PubChem CID 24762, "Ethylene glycol monostearate," Mar. 26, 2005, available <https://pubchem.ncbi.nlm.nih.gov/compound/24762> (30 pages).
PubChem CID 62238, "Cetostearyl alcohol," Aug. 8, 2005, available <https://pubchem.ncbi.nlm.nih.gov/compound/Cetostearyl-alcohol>(22 pages).
Final Report on the Safety Assessment of Steareth-2,-4,-6,-7,-10,-11,-13,-15, and-20. (1988). Journal of the American College of Toxicology. Published Nov. 1, 1988. 7(6), 881-910. https://doi.org/10.3109/10915818809078712.
Andersen, F. A. (1999). Final Report on the Safety Assessment of Ceteareth-2, -3, -4, -5, -6, -7, -8, -9, -10, -11, -12, -13, -14, -15, -16, -17, -18,-20,-22,-23,-24,-25,-27, -28, -29, -30, -33, -34, -40, -50, -55, -60, -80, and -100. International Journal of Toxicology. 18(3_suppl), 41-49. Published Apr. 1, 1999. https://doi.org/10.1177/109158189901800306.
Final Rejection for U.S. Appl. No. 16/890,044, dated Aug. 20, 2021 (15 pages).
Non-Final Rejection for U.S. Appl. No. 16/890,044, dated Apr. 19, 2021 (31 pages).
Non-Final Rejection for U.S. Appl. No. 16/890,044, dated Dec. 30, 2020 (22 pages).
Response to Non-Final Office Action for U.S. Appl. No. 16/890,044, filed Mar. 30, 2021 (8 pages).
Response to Non-Final Office Action for U.S. Appl. No. 16/890,044, filed Jul. 19, 2021 (5 pages).
International Search Report and Written Opinion for International Application No. PCT/US2021/032250, dated Sep. 14, 2021 (10 pages).

* cited by examiner

FIG. 2. Binary Dutasteride/Excipient Compatibility Study

| Excipient Mixed with Dutasteride | T=0 | | | | T=14 Days @ 50 °C | | | |
|---|---|---|---|---|---|---|---|---|
| | Dutasteride Assay (%w/w) | Impurities | | | Dutasteride Assay (%w/w) | Impurities | | |
| | | RRT | Related Peak Area Percent | Total Related Peak Area Percent | | RRT | Related Peak Area Percent | Total Related Peak Area Percent |
| Propylene Glycol | 0.040 | ND | ND | ND | 0.040 | ND | ND | ND |
| Diethylene Glycol Monoethylether | 0.052 | ND | ND | ND | 0.052 | ND | ND | ND |
| Laureth 4 | 0.059 | ND | ND | ND | 0.059 | ND | ND | ND |
| Polysorbate 20 | 0.013 | ND | ND | ND | 0.012 | ND | ND | ND |
| PEG-35 Castor Oil | 0.008 | ND | ND | ND | 0.009 | ND | ND | ND |
| Dimethyl Isosorbide | 0.038 | 0.14 | 2.54 | 6.00 | 0.033 | 0.35 | 0.17 | 9.49 |
| | | 0.18 | 2.14 | | | 0.54 | 0.24 | |
| | | 0.25 | 0.29 | | | 0.60 | 0.23 | |
| | | 0.33 | 0.30 | | | 0.82 | 8.07 | |
| | | 0.45 | 0.73 | | | 1.12 | 0.75 | |
| Isopropyl Myristate | 0.055 | ND | ND | ND | 0.055 | ND | ND | ND |
| Diethyl Sebacate | 0.021 | ND | ND | ND | < 0.005* | ND | ND | ND |
| Methyl Gluceth-20 | 0.008 | ND | ND | ND | 0.007 | 0.63 | 0.66 | 0.66 |
| Dehydrated Alcohol, 200 Proof | 0.079 | ND | ND | ND | 0.079 | ND | ND | ND |
| Olive Oil | 0.006 | ND | ND | ND | 0.006 | ND | ND | ND |
| Coconut Oil | 0.025 | ND | ND | ND | 0.025 | ND | ND | ND |
| Medium Chain Triglycerides | 0.027 | ND | ND | ND | 0.027 | ND | ND | ND |
| Glycerin | < 0.005 | ND | ND | ND | < 0.005 | ND | ND | ND |
| Castor Oil | 0.008 | ND | ND | ND | 0.009 | ND | ND | ND |

Note: Peak RRTs shifted from T0 due to method optimizations to improve detection of impurities.
* Extraction resulted in multiple layers (only ACN/H20 layer sampled) which may have contributed to the lower assay value at 14 days.

TOPICAL FORMULATIONS OF 5-α-REDUCTASE INHIBITORS AND USES THEREOF

CROSS-REFERENCE TO RELATED APPLICATIONS

This application claims priority to U.S. Provisional Application Ser. No. 62/757,483, filed Nov. 8, 2018, and U.S. Provisional Application Ser. No. 62/889,318, filed Aug. 20, 2019, both of which are herein incorporated by reference in their entirety for all purposes.

FIELD OF THE INVENTION

The invention relates to topical compositions for modulating hair growth and the treatment of various types of alopecia, for example, female and male androgenetic alopecia (AGA), alopecia areata, hair loss secondary to endocrine therapy in patients with breast cancer (Endocrine Therapy-Induced Alopecia or ETIA), and hirsutism.

BACKGROUND

The following description of the background of the invention is provided simply as an aid in understanding the invention and is not admitted to describe or constitute prior art to the invention.

Hair loss or alopecia is a common and embarrassing problem for many people. One of the most frequent types of alopecia is androgenetic alopecia, which is a common form of hair loss in both men and women. In men, this condition is also known as male-pattern baldness. The pattern of hair loss in women differs from male-pattern baldness. In women, the hair becomes thinner all over the head, and the hairline does not always recede. Researchers have determined that this form of hair loss is related to hormones called androgens, particularly an androgen called dihydrotestosterone (DHT).

Another common form of alopecia is hair loss secondary to endocrine therapy in patients with breast cancer (Endocrine Therapy-Induced Alopecia or ETIA). Selective Estrogen Receptor Modulators (SERMs) and Aromatase Inhibitors (AIs) currently hold an important place as adjuvant endocrine therapy for patients with early invasive or non-invasive, and/or advanced metastatic, hormone receptor-positive breast cancer. A substantial portion of the patients using SERMs, such as tamoxifen, for many years has reported hair loss or hair thinning. See Gallicchio, L. et al. "Aromatase inhibitor therapy and hair loss among breast cancer survivors." *Breast Cancer Res Treat* (2013) 142: 435-43. A retrospective questioning of patients with breast cancer regarding hair loss has revealed that approximately 34% of patients receiving endocrine therapy experience hair loss or thinning. See id. The psychosocial importance of alopecia resulting from cancer therapies cannot be understated. Approximately 58% of women receiving treatment for breast cancer state that alopecia is one of the most traumatic adverse events (AEs) during their treatment, with 8% indicating they would reject treatment because of this reaction alone. See Saagar, V. et al. "Alopecia with Endocrine Therapies in Patients with Cancer." *Oncologist* (2013) 18(10): 1126-34. Decreased Quality of Life (QoL), social activity, self-esteem, and body image are all associated with hair loss. See Wang, J. et al. "Protection Against Chemotherapy-Induced Alopecia." *Pharm Res.* (2006) 23(11): 2505-14 and Shapiro, J. "Hair Loss in Women." *N Engl J Med* (2007) 357(16) 1620-30. These findings have been attributed to the severe alopecia that develops during treatment with cytotoxic agents. Endocrine Therapy-Induced Alopecia (ETIA) that occurs during treatment with endocrine agents is of lower severity; however, ETIA can last for the duration of treatment (typically 5-10 years) which heightens and extends the impact on patients' QoL. ETIA has a significant negative impact on the QoL and often results in depression, anxiety and dissatisfaction with one's appearance and low self-esteem.

The properties of hair growth and the underlying mechanisms of AGA may help explain why SERMs and AIs cause ETIA. Animal (mice) models treated with a tamoxifen-loaded gel experienced arrested hair growth, with no growth persisting even after discontinuation of this treatment. See Bhatia, A. et al. "Tamoxifen-loaded liposomal topical formulation arrests hair growth in mice." *Br J Dermatol* (2010) 163(2): 412-15. Further, the affected hair follicles were arrested in the telogen phase. See id. Alopecia related to tamoxifen has been shown to exhibit a distribution similar to that of female AGA, primarily affecting the crown and frontal scalp. See Linder, J. et al. "Hair shaft abnormalities after chemotherapy and tamoxifen therapy in patients with breast cancer evaluated by optical coherence tomography." *Br J Dermatol* (2012) 167(6): 1272-78. Both men and women with AGA have lower levels of aromatase in hair follicles located within the frontal region of the scalp (see Sawaya, M. and Price, V. "Different Levels of 5α-Reductase Type I and II, Aromatase, and Androgen Receptor in Hair Follicles of Women and Men with Androgenetic Alopecia." *J Invest Dermatol* (1997) 109(3): 296-300.); therefore, it is possible that AIs mimic the hereditary deficiency typically seen in AGA.

Alopecia areata is a common autoimmune disorder, which results in unpredictable hair loss. Hair often falls out in small patches, e.g., around the size of a quarter. In more extreme cases, however, it can lead to complete hair loss on the scalp and even on the entire body.

In addition to alopecia, hirsutism, which is an excessive facial and/or body hair growth, particularly in women, is another common and embarrassing problem. Hirsutism can occur if the levels of female and male sex hormones become unbalanced with too high a proportion of male sex hormones (androgens) in women.

Researchers have attempted several treatment regimens to address different forms of alopecia and hirsutism with mixed results. For example, vasodilators such as potassium channel agonists including minoxidil and minoxidil derivatives such as diaminopyrimidine oxide; and an oral formulation of inhibitors for 5-α reductase enzyme that converts testosterone to DHT for the treatment of alopecia. Use of such oral formulations of such inhibitors such as oral finasteride has resulted in mixed success and with a risk of adverse side effects.

Avodart® (dutasteride) has been shown to be safe and effective for oral use through both extensive nonclinical testing and data obtained from over 18 years of clinical use. Dutasteride reduces circulating levels of DHT by inhibiting both type 1 and type 2 5α-reductase isoenzymes that are responsible for the conversion of testosterone to DHT, which is known to be the most potent natural androgen in the human body. DHT is believed to potently regulate the transcription of androgen-sensitive genes within the follicle, thereby affecting hair growth. See Jain, R. and De-Ekanumkul. "Potential targets in the discovery of new hair growth promoters for androgenic alopecia." *Expert Opin Ther Targets* (2014) 18(7): 787-086. Therefore, specific and systemic treatment with anti-5α-reductase agents (such as oral Avodart® (dutasteride) soft gelatin capsules, 0.5 mg) has been shown to treat hair loss on the scalp in both men and women. The fact that patients with deficiency of congenital 5α-reductase enzyme activity rarely experience AGA (see Herskovitz, I. and Tosti, A. "Female Pattern Hair Loss." *Int J Endocrinol Metab* (2013) 11(4): e9860 (published online Oct. 21, 2013), and that those patients using 5α-reductase enzyme inhibitors have a significant improvement in hair loss (see Olsen, E. et al. "The importance of dual 5α-reductase inhibition in the treatment of male pattern hair loss: Results of a randomized placebo-controlled study of dutasteride versus finasteride." *J Am Acad Dermatol* (2006) 55(6): 1014-23) are the objective preliminary evidence of this proposed indication. By contrast, given the systemic side effects of these agents when taken orally, topical 5α-reductase enzyme inhibitors can be locally (particularly frontal-temporal regions) or entirely applied on the scalp skin.

Oral finasteride and oral dutasteride are two of the most widely known and frequently used 5α-reductase inhibitors available today. Both drugs are designed to inhibit the conversion of testosterone into DHT. DHT is the androgen known to contribute to AGA. While oral finasteride and oral dutasteride share a few key benefits, they are both unique drugs with slightly different purposes and effects.

Between oral finasteride and oral dutasteride, oral finasteride is the older drug. Oral finasteride was developed in the 1970s and received FDA approval as a treatment for BPH in 1992. Oral finasteride was eventually approved for use as an AGA treatment in 1997 at a lower dose (1 mg) than the higher-dosed BPH treatment version of oral finasteride (5 mg). Dutasteride, on the other hand, was only patented in 1996 and became approved by the FDA as an oral treatment for BPH in 2001 at a dose of 0.5 mg.

Although oral dutasteride is approved as a treatment for AGA in some other countries, it still has not received FDA approval as a treatment for AGA in the United States.

In a study of 399 subjects, researchers found that oral dutasteride blocked 98.4%+/−1.2% of DHT at a 5 mg daily dose, compared to 70.8+/−18.3% with the same dose of oral finasteride. See Clark, R. V. et al. "Marked Suppression of Dihydrotestosterone in Men with Benign Prostatic Hyperplasia by Dutasteride, a Dual 5α-Reductase Inhibitor." *J Clin Endocrinol Metab* (2004) 89(5): 2179-84. This study was conducted on people suffering from BPH, meaning it used far higher doses of oral dutasteride and oral finasteride than the doses used to treat hair loss. Still, it shows that oral dutasteride is, milligram for milligram, more effective at lowering DHT than oral finasteride. It also shows that oral dutasteride is more consistent at blocking DHT than oral finasteride. The level of variability for the oral dutasteride group was +/−1.2%, showing an almost total elimination of DHT, with far less variation between patients than the +/−18.3% of the oral finasteride group. Study data also shows that oral dutasteride is more effective at promoting hair growth in people with male AGA than finasteride.

A 2006 study of 416 men shows that oral dutasteride produced better hair count results than oral finasteride over a period of 12 to 24 weeks. See Olsen, E. et al. 2006, supra. The researchers used an expert panel and before and after photographs to compare and verify the effects of the two drugs.

SUMMARY OF THE INVENTION

The present disclosure provides topical compositions of 5-α reductase inhibitors, such as dutasteride or finasteride or pharmaceutically acceptable salts, esters, or derivatives thereof for the treatment of hair loss secondary to endocrine therapy in patients with breast cancer (Endocrine Therapy-Induced Alopecia or ETIA), androgenetic alopecia (AGA), alopecia areata, and/or hirsutism. Specifically included within the scope of the invention are the compositions and formulations described in the working examples.

In one aspect, the present disclosure provides a topical composition comprising a therapeutically effective amount of 5-α reductase inhibitors, such as dutasteride or finasteride or pharmaceutically acceptable salts, esters, or derivatives thereof, and appropriate topical pharmaceutically acceptable excipients or carriers.

In another aspect of the invention, the present disclosure provides methods for preparing 5-α reductase inhibitor (e.g., dutasteride) formulations as set forth in the examples.

In another aspect, the present disclosure provides a method for stimulating the hair growth on the scalp of a human subject suspected of affected by endocrine-therapy induced alopecia from breast cancer treatment. The method includes a) providing a topical composition comprising a therapeutically effective amount of 5-α reductase inhibitors, such as dutasteride or finasteride or pharmaceutically acceptable salts, esters, or derivatives thereof, and appropriate topical pharmaceutically acceptable excipients or carriers; and b) topically applying the composition to the subject's skin or scalp on and/or adjacent to the area in which hair growth is desired. An increase in scalp hair density, hair thickness, or scalp coverage in the human subject receiving the topical composition as compared to an untreated individual is indicative of stimulation of hair growth on the scalp of the human subject.

In another aspect, the present disclosure provides a method for stimulating the hair growth on the scalp of a human subject suspected of being affected by androgenetic alopecia. The method includes a) providing a topical composition comprising a therapeutically effective amount of 5-α reductase inhibitors, such as dutasteride or finasteride or pharmaceutically acceptable salts, esters, or derivatives thereof, and appropriate topical pharmaceutically acceptable excipients or carriers; and b) topically applying the composition to the subject's skin or scalp on and/or adjacent to the area in which hair growth is desired. An increase in scalp hair density, hair thickness, or scalp coverage in the human subject receiving the topical composition as compared to an untreated individual is indicative of stimulation of hair growth on the scalp of the human subject.

In another aspect, the present disclosure provides a method for reducing the facial hair growth of a human subject suspected of being affected by hirsutism. The method includes a) providing a topical composition comprising a therapeutically effective amount of 5-α reductase inhibitors, such as dutasteride or finasteride or pharmaceutically acceptable salts, esters, or derivatives thereof, and appropriate topical pharmaceutically acceptable excipients or carriers; and b) topically applying the composition to the subject's facial or body skin on and/or adjacent to the area in which reduced hair growth is desired. A decrease in facial hair density, hair thickness, or coverage in the human subject receiving the topical composition as compared to an untreated individual is indicative of a reduction of facial hair growth of the human subject.

In another aspect, the present disclosure provides a topical formulation comprising a therapeutically effective amount of dutasteride or a pharmaceutically acceptable salt, ester, or derivative thereof dissolved in an oil phase; and a topical pharmaceutically acceptable excipient or carrier. The topical formulation may be an emulsion. The oil phase may include at least one oil, alternatively at least two oils. The formulation may further include a humectant, a thickener, an emulsifier, and a preservative.

In another aspect, the present disclosure provides a topical formulation comprising a therapeutically effective amount of dutasteride or a pharmaceutically acceptable salt, ester, or derivative thereof dissolved in an oil phase; and a topical pharmaceutically acceptable excipient or carrier. The formulation may not contain ethyl alcohol and/or polypropylene glycol.

In another aspect, the present disclosure provides a topical formulation comprising a therapeutically effective amount of dutasteride or a pharmaceutically acceptable salt, ester, or derivative thereof dissolved in an aqueous phase; and a topical pharmaceutically acceptable excipient or carrier. The topical formulation may be an emulsion. The aqueous phase may optionally include a solubilizer. The aqueous phase may optionally include a penetration enhancer. The formulation may further include a thickener, an emollient, a pH adjuster, a preservative, and/or a conditioning agent.

In another aspect, the present disclosure provides methods for preparing a topical formulation, comprising the steps of mixing a conditioning agent with water to form a conditioning solution; mixing a first emulsifier, a first preservative, and a solvent to obtain an emulsifier solution; mixing dutasteride, at least one oil, and at least one solvent to obtain a dutasteride solution; mixing the dutasteride solution with the emulsifier solution to obtain a combined solution; mixing the combined solution with the conditioning solution to form a dutasteride conditioning mixture; and mixing a second emulsifier and a second preservative into the dutasteride conditioning mixture.

In another aspect, the present disclosure provides methods for preparing a topical formulation, comprising the steps of mixing a humectant with water to form a humectant solution; mixing a thickener and a first solvent to form a thickener solution; mixing the thickener solution with the humectant solution to form a combined solution; mixing a preservative into the combined solution to form a combined preservative solution; mixing dutasteride and a second solvent to form a dutasteride solution; mixing at least one oil into the dutasteride solution to form a dutasteride oil mixture; mixing at least one emulsifier to the dutasteride oil mixture to form a second dutasteride oil mixture; and mixing the second dutasteride oil mixture with the combined preservative solution in a vessel.

In some embodiments of the above aspects, the therapeutically effective amount of dutasteride is about 0.001% to about 1% (w/w). In some embodiments, the therapeutically effective amount of 5-α reductase inhibitors, such as dutasteride or finasteride, is about 0.001% to about 0.5% (w/w). In some embodiments, the therapeutically effective amount of 5-α reductase inhibitors, such as dutasteride or finasteride, is about 0.002% to about 0.1% (w/w). In some embodiments, the therapeutically effective amount of dutasteride is about 0.001%, 0.005%, 0.010%, 0.025%, 0.050%, 0.075%, 0.100%, 0.150%, 0.200%, 0.250%, 0.300%, 0.350%, 0.400%, 0.500%, 0.600%, 0.700%, 0.800%, 0.900% or about 1% (w/w). In some embodiments, the amount of 5-α reductase inhibitors, such as dutasteride or finasteride, administered in a single topical application is about: 0.01 mg, 0.05 mg, 0.1 mg, 0.25 mg, 0.5 mg, 0.75 mg, 1 mg, 1.25 mg, 1.5 mg, 2 mg, 2.5 mg, 3 mg, 3.5 mg, 4 mg, 4.5 mg, or 5 mg. In some embodiments, the amount of 5-α reductase inhibitors, such as dutasteride or finasteride, administered in a single topical application is about 0.1 to about 3.0 mg, alternatively about 0.3 mg to about 2.5 mg, alternatively about 0.5 mg to about 2.5 mg, alternatively about 0.5 mg to about 2.0 mg, alternatively about 0.5 mg to about 1.5 mg, alternatively about 0.5 mg to about 1.0 mg.

In some embodiments, the dutasteride of the composition is in the form of nanoparticles. In some embodiments, the nanoparticles are coated with 5-α reductase inhibitors, such as dutasteride or finasteride. In some embodiments, the 5-α reductase inhibitors, such as dutasteride or finasteride, is slowly released to the skin or scalp when the topical composition is applied to the skin or scalp of the human subject. In some embodiments, the diameter of the nanoparticles is about 25 nm to about 500 nm. In some embodiments, the diameter of the nanoparticles is about 100 nm to about 500 nm. In some embodiments, the diameter of the nanoparticles is about 500 nm.

In some embodiments of the above aspects, the topical composition comprises a surfactant, a co-surfactant, a penetration enhancer, an antioxidant, a buffering agent, a preservative, a viscosity modifying agent, a chelating or complexing agent, a coloring agent, a perfume, a polymer, a gelling agent, an alcohol, a liquid or semi-solid oily component, or any combination thereof.

In some embodiments, the topical composition comprises at least two of API (5-α reductase inhibitors, such as dutasteride or finasteride), cationic emulsifier, conditioning agent, emollient, emulsifier, humectant solvent, nonionic emulsifier, penetration enhancer, pH adjuster, preservative, solvent, thickener, viscosity enhancer, or any combination thereof.

In some embodiments, the topical composition is a cream and comprises a solvent, a humectant, a thickener, a preservative, an emollient, an emulsifier, and a penetration enhancer.

In some embodiments, the topical composition is a lotion and comprises a solvent, a humectant, a thickener, a preservative, an emollient, an emulsifier, and a penetration enhancer.

In some embodiments, the topical composition is a lotion and comprises a solvent, a humectant, a thickener, a preservative, an emollient, an emulsifier, a pH adjuster, and a penetration enhancer.

In some embodiments, the topical composition is a lotion conditioner and comprises a solvent, a humectant, a thickener, a preservative, an emollient, an emulsifier, and a conditioning agent.

In some embodiments, the topical composition is a lotion serum and comprises a solvent, a humectant, a thickener, a preservative, an emollient, an emulsifier, a pH adjuster, a penetration enhancer, and a conditioning agent.

In some embodiments, the topical composition is a gel and comprises a solvent, a thickener, an emollient, and a penetration enhancer.

In some embodiments, the topical composition is a gel and comprises a solvent, a thickener, and a penetration enhancer.

In some embodiments, the topical composition is a gel and/or serum and comprises a solvent, a viscosity enhancer, an emollient, and a penetration enhancer.

In some embodiments of the above aspects, the topical pharmaceutically acceptable carrier is hydrophilic, hydrophobic, lipophilic, or amphiphilic, or a mixture thereof. In some embodiments, the pharmaceutically acceptable carrier comprises a hydrophobic or lipophilic substance comprising a paraffin oil, an ester of a $C_8$-$C_{18}$ organic acid, a $C_8$-$C_{30}$ fatty alcohol, a silicone oil, a vegetable oil, a fractionated or hydrogenated vegetable oil, a monoglyceride, a diglyceride, a triglyceride, a phospholipid, dimethylisosorbide, a volatile solvent, N-methylpyrrolidone, dimethylacetamide, dimethylformamide; dimethylsulphoxide, or any combination thereof. In some embodiments, the topical pharmaceutically acceptable excipients or carriers comprise ethanol, polypropylene glycol, purified water, or a combination thereof.

In some embodiments of the above aspects, the topical composition is in the form of foam, cream, paste, gel, aerosol, powder, oil, serum, or liquid. In some embodiments, the topical composition further comprises a therapeutically effective amount of finasteride, minoxidil, or a combination thereof. In some embodiments, the amount of finasteride can be about 0.01 mg to about 5 mg. In some embodiments, the amount of finasteride can be about: 0.01 mg, 0.05 mg, 0.1 mg, 0.25 mg, 0.5 mg, 0.75 mg, 1 mg, 1.25 mg, 1.5 mg, 2 mg, 2.5 mg, 3 mg, 3.5 mg, 4 mg, 4.5 mg, or 5 mg. In some embodiments, the amount of minoxidil can be about: 0.01 mg, 0.05 mg, 0.1 mg, 0.25 mg, 0.5 mg, 0.75 mg, 1 mg, 1.25 mg, 1.5 mg, 2 mg, 2.5 mg, 3 mg, 3.5 mg, 4 mg, 4.5 mg, 5 mg, 5.5 mg, 6.0 mg, 6.5 mg, 7.0 mg. or 7.5 mg. In some embodiments, the topical composition comprises a propellant. Non-limiting examples of propellant include dichloromethane, dimethyl ether, butanes, propane, nitrogen, fluorocarbons, and carbon dioxide.

In some embodiments, the topical composition is applied to the skin or scalp of a human subject for a single day. In some embodiments, the topical composition is applied to the skin or scalp of a human subject for multiple days. In some embodiments, the topical composition is applied each day for about 2, 3, 4, 5, 6, 7, 8, 9, 10, 11, 12, 13, 14, or 21 or more days. In some embodiments, the topical composition is applied each day for 2, 3, 4, 5, 6, 7, 8, 9, 10, 11, 12, 13, 14, 15, 16, or more weeks. In some embodiments, the topical 5-α reductase inhibitor formulation is applied QD, bid, tid, qid, or more frequently. In some embodiments, the topical composition is applied multiple times each day for multiple days or multiple weeks, or multiple months. In some embodiments, the skin is abdominal skin. In some embodiments, the skin is skin on the limbs, forehead, throat, or back.

In some embodiments, stimulating the hair growth comprises an increase in hair count. In some embodiments, stimulating the hair growth comprises hair thickness increase. In some embodiments, the hair thickness increase comprises an increase in frontal, central, vertex regions, or their combination of the scalp of the human subject. In some embodiments, stimulating the hair growth comprises improved scalp coverage and improved hair structure.

In some embodiments of the above aspects, the human subject can be a male or a female. In some embodiments, the human subject suspected of being affected by androgenetic alopecia is a male. In some embodiments, the male suspected of being affected by androgenetic alopecia has male baldness pattern.

As used herein, unless otherwise stated, the singular forms "a," "an," and "the" include plural reference. Thus, for example, a reference to "a protein" includes a plurality of protein molecules.

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

The summary of the disclosure described above is non-limiting and other features and advantages of the disclosed apparatus and methods will be apparent from the following detailed description of the disclosure, and from the claims. It is to be understood that other 5-α reductase inhibitors, such as finasteride, may be substituted for dutasteride in any of the formulations and methods.

BRIEF DESCRIPTION OF THE DRAWINGS

FIG. 2 shows the results of the binary dutasteride/excipient compatibility study.

DETAILED DESCRIPTION

Figure 1:
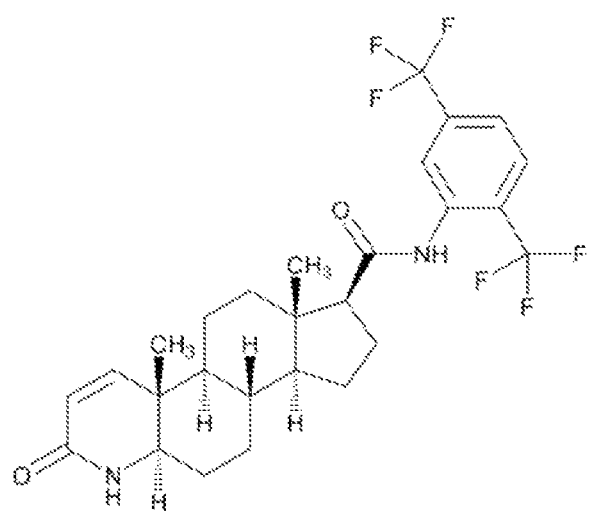
FIG. 1 shows the chemical structure of dutasteride.

The present disclosure is directed to topical compositions of 5-α reductase inhibitors, such as dutasteride or finasteride or pharmaceutically acceptable salts, esters, or derivatives thereof for the treatment of hair loss secondary to endocrine therapy in patients with breast cancer (Endocrine Therapy-Induced Alopecia or ETIA), androgenetic alopecia (AGA), Alopecia Areata (AA), and hirsutism. The topical composition of 5-α reductase inhibitors is advantageous over any oral formulation of 5-α reductase inhibitors because it may allow for a slow release of the active ingredient, better penetration at the therapeutically effective amount of the 5-α reductase inhibitor with an improved safety profile since it does not need to travel through the bloodstream to be efficacious, thereby minimizing the risk of systemic side effects.

Dutasteride is chemically designated as (5α,17β)-N-[2,5 bis(trifluoromethyl)phenyl]-3-oxo-4-azaandrost-1-ene-17-carboxamide. The empirical formula of dutasteride is $C_{27}H_{30}F_6N_2O_2$, representing a molecular weight of 528.53 kDa with the following structural formula as shown in FIG. 1. Dutasteride is a selective inhibitor of both the type 1 and type 2 5α-reductase isoenzymes, an intracellular enzyme that converts testosterone to DHT. Additionally, dutasteride may be more effective than another known type 1 5α-reductase inhibitor finasteride because dutasteride inhibits both type 1 and type 2 5α-reductase isoenzymes.

Although dutasteride may be more potent than finasteride in inhibiting 5α-reductase enzymes, they both have published adverse effects. Oral formulations of finasteride and dutasteride have been shown by researchers to be effective in treating androgenetic alopecia (AGA), and proposed as a treatment for hair loss secondary to endocrine therapy in patients with breast cancer (Endocrine Therapy-Induced Alopecia or ETIA). Oral dutasteride has not been approved for any form of treatment of alopecia or hirsutism in the United States.

The present invention provides topical formulations of 5-α reductase inhibitors, such as dutasteride or finasteride or pharmaceutically acceptable salts, esters, or derivatives thereof for the treatment of hair loss secondary to endocrine therapy in patients with breast cancer (Endocrine Therapy-Induced Alopecia or ETIA), androgenetic alopecia (AGA), and hirsutism that is safe and effective because the topical formulation may allow for: a slow release of the active ingredient; better penetration at the therapeutically effective amount of the 5-α reductase inhibitor; and an improved safety profile since it does not need to travel through the bloodstream to be efficacious, thereby minimizing the risk of systemic side effects.

As used herein the term "modulating hair growth" refers to an increase or decrease of hair count, hair thickness, or hair structure in scalp or face.

As used herein the term "therapeutically effective amount" is a sufficient to contribute to the treatment, prevention, or reduction of a symptom or symptoms of a disease. A reduction of a symptom or symptoms (and grammatical equivalents of this phrase) means decreasing of the severity or frequency of the symptom(s), or elimination of the symptom(s).

As used herein, the amount of a dutasteride, when expressed as "%" refers to % (w/w) unless otherwise indicated.

As used herein, the phrase "pharmaceutically acceptable" is used with reference to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the term "penetration enhancement" or "permeation enhancement" means an increase in the permeability of a biological membrane (i.e. skin or mucosa) to a drug, so as to increase the rate at which the drug is transported through the membrane. "Permeation enhancer", "enhancer", "penetration enhancer", or similar terms mean a material that achieves such permeation or penetration enhancement, and an "effective amount" of an enhancer means an amount effective to enhance penetration through the skin or mucosa of a selected agent to a desired degree.

Suitable penetration enhancers that can be used in the present invention include, but are not limited to: sulfoxides such as dimethylsulfoxide (DMSO) and decylmethylsulfoxide ($C_{10}$ MSO); ethers such as diethylene glycol monoethyl ether (available commercially as TRANSCUTOL® P) and diethylene glycol monomethyl ether; 1-substituted azacycloheptan-2-ones, such as 1-n-dodecyl-cyclazacycloheptan-2-one; alcohols such as propanol, octanol, benzyl alcohol, and the like; fatty acids such as lauric acid, oleic acid, and valeric acid; fatty acid esters such as isopropyl myristate, isopropyl palmitate, methylpropionate, and ethyl oleate; polyol esters such as butanediol and polyethylene glycol monolaurate; amides and other nitrogenous compounds such as urea, N,N-dimethylacetamide (DMA), N,N-dimethylformamide (DMF), 2-pyrrolidone, 1-methyl-2-pyrrolidone, ethanolamine, diethanolamine, and triethanolamine; terpenes and terpinoids; alkanones; organic acids, such as salicylic acid and salicylates, citric acid and succinic-acid and the like; and any mixtures thereof. Suitable penetration enhancers also include, but are not limited to, medium chain triglycerides, isopropyl myristate, diisopropyl adipate, isopropyl palmitate, propylene glycol, diethylene glycol monoethylether (TRANSCUTOL® P), oleyl alcohol, dehydrated alcohol, benzyl alcohol, laureth-4, diethyl sebacate, and dimethyl isosorbide.

Suitable solvents that can be used in the present invention include, but are not limited to: sterile water, glycerin, medium chain triglycerides, isopropyl myristate, diisopropyl adipate, isopropyl palmitate, propylene glycol, olive oil, castor oil, coconut oil, light mineral oil, diethylene glycol monoethylether (TRANSCUTOL® P), diethyl sebacate, benzyl alcohol, cyclomethicone, PEG 400, dehydrated alcohol, and dimethyl isosorbide.

Suitable humectants that can be used in the present invention include, but are not limited to: sodium hyaluronate, glycerin, sorbitol solution, 70%, and methyl gluceth-20 (GLUCAM® E20).

Suitable thickeners that can be used in the present invention include, but are not limited to: xanthan gum, cetearyl alcohol, PROMULGEN® D, CARBOPOL® 974P NF Polymer, PEMULEN® TR-2, PEMULEN® TR-1, KLUCEL® HG Pharm, CARBOPOL® 980 NF, Polymer, and SEPINEO® P 600.

Suitable preservatives that can be used in the present invention include, but are not limited to: methylparaben and propylparaben.

Suitable emollients that can be used in the present invention include, but are not limited to: olive oil, medium chain triglycerides, isopropyl myristate, diisopropyl adipate, isopropyl palmitate, castor oil, light mineral oil, cyclomethicone, diethyl sebacate, benzyl alcohol, PEG-35 castor oil, and coconut oil.

Suitable emulsifiers that can be used in the present invention include, but are not limited to: BRIJ® L4, ARLACEL® 165, TWEEN® 20, BRIJ® 5721, BRIJ® S2, PROMULGEN® D, Stearalkonium Chloride, PEMULEN® TR-2, PEMULEN® TR-1, Sodium Monostearate, SEPINEO® P 600, Laureth-4, Polysorbate 20, Sorbitan Monostearate, and PEG-35 Castor Oil. Non-ionic emulsifiers include, but are not limited to, BRIJ® L4, ARLACEL® 165, Sodium Monostearate, Laureth-4, Polysorbate 20, and PEG-35 Castor Oil. Cationic surfactants include, but are not limited to, stearalkonium chloride.

Suitable pH adjusters that can be used in the present invention include, but are not limited to: NaOH and HCl solutions.

Suitable conditioning agents that can be used in the present invention include, but are not limited to: stearalkonium chloride and Polyquaternium-10.

Suitable solubilizers that can be used in the present invention include, but are not limited to: Laureth-4.

Suitable viscosity enhancers that can be used in the present invention include, but are not limited to: PEG 3350.

EXAMPLES

Example 1: Topical Formulation Comprising Dutasteride

A topical formulation of 0.10% w/v may be prepared as follows.

| Ingredient | Final Concentration | Amount per 30 ml |
|---|---|---|
| Dutasteride | 0.10% | 0.030 g |
| Ethyl Alcohol (95%) | 55.00% (v/v) | 16.50 ml |
| Polypropylene glycol | 5.00% (v/v) | 1.50 ml |
| Purified Water | 39.90% (v/v) | 11.97 ml |
| TOTAL | 100.00% | 30.00 ml |

Example 2: Topical Cream Formulations Comprising Dutasteride (Dutasteride Dissolved in Oil Phase)

A. A topical formulation of 0.05% w/w may be prepared as follows:

| Phase | Ingredients | % w/w | IID Topical Max (% w/w) | Category |
|---|---|---|---|---|
| A | Sterile Water for Irrigation | q.s. to 100 (64.15) | 100.00 | Solvent |
| B | Sodium Hyaluronate | 0.10 | 2.50 | Humectant |
| C | Glycerin | 5.00 | 20.00 | Humectant Solvent |
|   | Xanthan Gum | 0.50 | 2.85 | Thickener |
| D | Methylparaben | 0.18 | 0.50 | Preservative |
| E | Olive Oil | 3.00 | 27.75 | Emollient |
|   | Medium Chain Triglycerides | 10.00 | 15.00 | Solvent Emollient Penetration Enhancer |
|   | Isopropyl Myristate | 10.00 | 50.30 | Solvent Emollient Penetration Enhancer |
|   | BRIJ ® L4 | 1.00 | 5.22 | Emulsifier |
|   | Dutasteride | 0.05 | N/A | API |
| F | ARLACEL ® 165 | 4.00 | 7.50 | Emulsifier |
|   | Cetearyl Alcohol | 2.00 | 12.00 | Thickener |
|   | Propylparaben | 0.02 | 5.25 | Preservative |
|   | Total | 100.00 | | |

The components of Phase A were combined in the main vessel until a solution was obtained. With high agitation, Phase B was sprinkled into the main vessel and mixed until a homogenous gel was obtained. Phase C was pre-mixed in a separate container and added to the main vessel until it was uniformly dispersed. The batch was then heated to 70-75° C. Phase D was then added to the main vessel and mixed until Phase D was solubilized. The components of Phase E were combined in a separate vessel and mixed until a solution was obtained. Phase F was then added to Phase E in the separate vessel and heated until the mixture was 70-75° C.

The When the mixture in the main vessel and the Phase E+F mixture are both at 70-75° C., Phase E+F was added to the main vessel for homogenization. The batch was then cooled down to less than 30° C.

The Hydrophilic-lipophilic balance (HLB), which is the balance of the size and strength of the hydrophilic and lipophilic moieties of a surfactant molecule, was calculated.

| Ingredient | HLB | % w/w | Ingredient | Required HLB | % w/w |
|---|---|---|---|---|---|
| ARLACEL ® 165 | 11.00 | 4.00 | Olive Oil | 7.70 | 3.00 |
| BRIJ ® 4 | 9.70 | 1.00 | MCT | 10.00 | 10.00 |
|   |   |   | Isopropyl Myristate | 11.50 | 10.00 |
|   |   |   | Cetearyl Alcohol | 15.50 | 2.00 |
| Total HLB/ Total % w/w | 10.74 | 5.00 | Total Required HLB/Total % W/W | 10.76 | 25.00 |

B. A topical formulation of 0.05% w/w may be prepared as follows. (2019-045-31R)

| Phase | Ingredients | % w/w | IID Topical Max (% w/w) | Category |
|---|---|---|---|---|
| A | Sterile Water for Irrigation | q.s. to 100 (46.35) | 100.00 | Solvent |
| B | Sodium Hyaluronate | 0.10 | 2.50 | Humectant |
| C | Glycerin | 5.00 | 20.00 | Humectant Solvent |
|   | Xanthan Gum | 0.50 | 2.85 | Thickener |
| D | Methylparaben | 0.18 | 0.50 | Preservative |
| E | Diisopropyl Adipate | 20.00 | 20.00 | Solvent Emollient Penetration Enhancer |
|   | Medium Chain Triglycerides | 15.00 | 15.00 | Solvent Emollient Penetration Enhancer |
|   | Isopropyl Palmitate | 7.30 | 7.30 | Solvent Emollient Penetration Enhancer |
|   | BRIJ ® L4 | 2.00 | 5.22 | Nonionic Emulsifier |
|   | Dutasteride | 0.05 | N/A | API |
| F | ARLACEL ® 165 | 1.00 | 7.50 | Nonionic Emulsifier |
|   | Cetearyl Alcohol | 2.50 | 12.00 | Thickener |
|   | Propylparaben | 0.02 | 5.25 | Preservative |
|   | Total | 100.00 | | |

The components of Phase A were combined in the main vessel until a solution was obtained. With high agitation, Phase B was sprinkled into the main vessel and mixed until a homogenous gel was obtained. Phase C was pre-mixed in a separate container and added to the main vessel until it was uniformly dispersed. The batch was then heated to 70-75° C. Phase D was then added to the main vessel and mixed until Phase D was solubilized. The components of Phase E were combined in a separate vessel and mixed until a solution was obtained. Phase F was then added to Phase E in the separate vessel and heated until the mixture was 70-75° C. When the mixture in the main vessel and the Phase E+F mixture are both at 70–75° C., Phase E+F was added to the main vessel for homogenization. The batch was then cooled down to less than 30° C.

The Hydrophilic-lipophilic balance (HLB), which is the balance of the size and strength of the hydrophilic and lipophilic moieties of a surfactant molecule, was calculated.

| Ingredient | HLB | % w/w | Ingredient | Required HLB | % w/w |
|---|---|---|---|---|---|
| BRIJ® L4 | 9.70 | 2.00 | Diisopropyl Adipate | 9.00 | 20.00 |
| ARLACEL® 165 | 11.00 | 1.00 | Medium Chain Triglycerides | 10.00 | 15.00 |
| | | | Isopropyl Palmitate | 11.50 | 7.30 |
| | | | Cetearyl Alcohol | 15.50 | 2.50 |
| Total HLB/ Total % W/W | 10.13 | 3.00 | Total Required HLB/Total % W/W | 10.10 | 44.80 |

Example 3: Topical Cream Formulation Comprising Dutasteride (Dutasteride Dissolved in Water Phase)

A topical formulation of 0.05% w/w may be prepared as follows.

| Phase | Ingredients | % w/w | IID Topical Max (% w/w) | Category |
|---|---|---|---|---|
| A | Sterile Water for Irrigation | q.s. to 100 (63.55) | 100.00 | Solvent |
| | TWEEN® 20 | 1.00 | 15.00 | Emulsifier |
| B | Propylene Glycol | 5.00 | 99.98 | Solvent Penetration Enhancer |
| | Methylparaben | 0.18 | 0.50 | Preservative |
| | Propylparaben | 0.02 | 5.25 | Preservative |
| C | BRIJ® S721 | 2.00 | 3.00 | Emulsifier |
| | BRIJ® S2 | 2.00 | 5.00 | Emulsifier |
| | Castor Oil | 5.00 | 14.90 | Solvent Emollient |
| | Light Mineral Oil | 2.00 | 43.40 | Solvent Emollient |
| | Cyclomethicone | 3.00 | 13.00 | Emollient |
| | Cetearyl Alcohol | 1.00 | 12.00 | Thickener |
| D | SEPINEO® P 600 | 0.20 | 4.00 | Thickener Emulsifier |
| E | TRANSCUTOL® P | 15.00 | 49.91 | Solvent Penetration Enhancer |
| | Dutasteride | 0.05 | — | API |
| | Total | 100.00 | | |

The components of Phase A were combined in the main vessel. The components of Phase B were combined in a separate vessel and mixed until a solution was obtained. Phase B was then added to the main vessel and mixed until a solution was obtained. The main vessel was then heated to 70-75° C. The components of Phase C were mixed in a separate vessel and heated to 70-75° C. Phase C was then added to the main vessel with homogenization. The contents of the main vessel were mixed until the oil phase was fully incorporated. Phase D was then added to the main vessel and homogenized until the batch temperature was 60° C. The main vessel was cooled down to <30° C. Phase E was combined in a separated container until a solution was obtained. Phase E was then added to the main vessel and mixed.

The HLB was Calculated.

| Ingredient | HLB | % w/w | Ingredient | Required HLB | % w/w |
|---|---|---|---|---|---|
| BRIJ® S2 | 4.90 | 2.00 | Castor Oil | 14.00 | 10.00 |
| BRIJ® S721 | 15.50 | 2.00 | Light Mineral Oil | 10.00 | 5.00 |
| TWEEN® 20 | 16.70 | 1.00 | Cyclomethicone | 7.50 | 5.00 |
| | | | Cetearyl Alcohol | 15.50 | 1.00 |
| Total HLB | 11.50 | 5.00 | Total Req HLB | 11.57 | 21.00 |

Example 4: Topical Lotions ("Conditioners") Comprising Dutasteride (Dutasteride Dissolved in Oil Phase)

A topical formulation of 0.05% w/w for a leave-in conditioner may be prepared as follows.

| Phase | Ingredients | % w/w | IID Topical Max (% w/w) | Category |
|---|---|---|---|---|
| A | Sterile Water for Irrigation | q.s. to 100 (50.00) | 100.00 | Solvent |
| | Stearalkonium Chloride | 1.50 | 3.15 | Conditioning Agent |
| | Methylparaben | 0.18 | 0.50 | Preservative |
| | Glycerin | 5.00 | 20.00 | Humectant Solvent |
| B | Olive Oil | 3.00 | 27.75 | Emollient |
| | Diethyl Sebacate | 20.00 | 24.00 | Solvent Emollient |
| | Dutasteride | 0.05 | — | API |
| C | PROMULGEN® D | 5.00 | 8.00 | Emulsifier Thickener |
| | Propylparaben | 0.02 | 5.25 | Preservative |
| D | Sterile Water for Irrigation | 15.00 | 100.00 | Solvent |
| | Polyquaternium-10 | 0.25 | 2.06 | Conditioning Agent |
| | Total | 100.00 | | |

The components of Phase A were combined in the main vessel while heating to 70-75° C. The components were mixed until uniform. The components of Phase B was combined in a separate vessel and mixed until a solution was obtained. The components of Phase C were added to Phase B while heating up to 70-75° C. The combined Phases B and C were added to the main vessel while heating at 70-75° C. and mixed until uniform. The main vessel was then cooled to 40° C. The components of Phase D were combined in a separate vessel. Phase D was then added to the main vessel and the main vessel was then cooled to <30° C.

A topical formulation of 0.05% w/w for a leave-in conditioner may be prepared as follows. (2019-045-34R)

| Phase | Ingredients | % w/w | IID Topical Max (% w/w) | Category |
|---|---|---|---|---|
| A | Sterile Water for Irrigation | q.s. to 100 (44.55) | 100.00 | Solvent |
|  | Polyquaternium-10 | 0.20 | 2.06 | Conditioning Agent |
| B | Stearalkonium Chloride | 0.50 | 3.15 | Cationic Emulsifier Conditioning Agent |
|  | Methylparaben | 0.18 | 0.50 | Preservative |
|  | Glycerin | 5.00 | 20.00 | Humectant Solvent |
| C | Olive Oil | 9.00 | 27.75 | Emollient |
|  | Benzyl Alcohol | 0.50 | 2.70 | Solvent Emollient |
|  | Medium Train Triglycerides | 15.00 | 15.00 | Solvent Emollient Penetration Enhancer |
|  | Diisopropyl Adipate | 20.00 | 20.00 | Solvent Emollient Penetration Enhancer |
|  | Dutasteride | 0.05 | — | API |
| D | PROMULGEN® D | 5.00 | 8.00 | Emulsifier Thickener |
|  | Propylparaben | 0.02 | 5.25 | Preservative |
|  | Total | 100.00 |  |  |

The components of Phase A were combined in the main vessel while heating to 70-75° C. The components were mixed until uniform. The components of Phase B combined in a separate vessel and mixed until a solution was obtained. The components of Phase C were combined in a separate vessel and mixed until a solution was obtained. The components of Phase C were added to Phase B while heating up to 70-75° C. The combined Phases B and C were added to the main vessel while heating at 70-75° C. and mixed until uniform. The main vessel was then cooled to 40° C. The components of Phase D were combined in a separate vessel. Phase D was then added to the main vessel and the main vessel was then cooled to <30° C.

Example 5: Topical Lotion Formulation Comprising Dutasteride (Dutasteride Dissolved in Water Phase)

A topical formulation of 0.05% w/w for application may be prepared as follows.

| Phase | Ingredients | % w/w | IID Topical Max (% w/w) | Category |
|---|---|---|---|---|
| A | Sterile Water for Irrigation | q.s. to 100 (54.45) | 100.00 | Solvent |
|  | Propylene Glycol | 5.00 | 99.98 | Solvent Penetration Enhancer |
|  | Sorbitol Solution, 70% | 5.00 | 36.80 | Humectant |
|  | Dutasteride | 0.05 | — | API |
| B | CARBOPOL® 974P NF Polymer | 0.20 | 1.51 | Thickener |
|  | PEMULEN® TR-2 | 0.10 | 0.60 | Thickener Emulsifier |
| C | Propylene Glycol | 5.00 | 99.98 | Solvent Penetration Enhancer |
|  | Methylparaben | 0.18 | 0.50 | Preservative |
|  | Propylparaben | 0.02 | 5.25 | Preservative |
| D | Cyclomethicone | 3.00 | 13.00 | Solvent Emollient |
|  | Castor Oil | 5.00 | 14.90 | Solvent Emollient |
| E | 10% NaOH Solution | q.s. to pH 6.5-7.0 | pH adjuster | pH adjuster |
|  | Sterile Water for Irrigation | (5.00) | 100.00 | Solvent |
| F | Sterile Water for Irrigation | 15.00 | 100.00 | Solvent |
|  | Polyquaternium-10 | 2.00 | 2.06 | Conditioning Agent |
|  | Total | 100.00 |  |  |

The components of Phase A were combined in the main vessel and were mixed until a solution was obtained. The components of Phase B were sprinkled into the main vessel with vigorous mixing for no longer than 30 minutes. The components of Phase C were combined in a separate container and mixed until a solution was obtained. Phase C was added to the main vessel and mixed until uniform. The components of Phase D were pre-mixed and then added to the main vessel with vigorous mixing and mixed until fully incorporated. The pH of the mixture in the main vessel was adjusted to pH 6.5-7.0 using the Phase E. The components of Phase F were combined in a separate container and mixed until a solution was obtained, added to the main vessel, and mixed until uniform.

Example 6: Topical Lotion Formulation Comprising Dutasteride (2019-045-71)

A topical formulation of 0.05% w/w for application may be prepared as follows.

| Phase | Ingredients | % w/w | IID Topical Max (% w/w) | Category |
|---|---|---|---|---|
| A | Sterile Water for Irrigation | 43.20 | 100.00 | Solvent |
|  | Glycerin | 3.00 | 20.00 | Humectant Solvent |
|  | Methylparaben | 0.18 | 0.50 | Preservative |
| B | CARBOPOL® 974P Polymer | 0.10 | 1.51 | Thickener |
| C | Oleyl Alcohol | 4.00 | 10.00 | Penetration Enhancer |
|  | Isopropyl Myristate | 20.45 | 35.00 | Solvent Emollient Penetration Enhancer |
|  | Diethyl Sebacate | 24.00 | 24.00 | Solvent Emollient Penetration Enhancer |
|  | Dutasteride | 0.05 | — | API |
| D | Propylparaben | 0.02 | 5.25 | Preservative |
|  | BRIJ® S2 | 1.50 | 5.00 | Nonionic Emulsifier |
|  | BRIJ® S721 | 2.00 | 3.00 | Nonionic Emulsifier |
|  | Cetearyl Alcohol | 1.00 | 12.00 | Thickener |
| E | Sterile Water for Irrigation | 0.50 | 100.00 | Solvent |

| Phase | Ingredients | % w/w | IID Topical Max (% w/w) | Category |
|---|---|---|---|---|
| F | 10% NaOH Solution | q.s. to pH 5.5-6.0 | Adj pH | pH adjuster |
| G | Sterile Water for Irrigation | q.s. to 100 | 100.00 | Solvent |
|   | Total | 100.00 |   |   |

The components of Phase A were combined in the main manufacturing vessel and heated to 70-75° C., if necessary, to dissolve methylparaben. Phase B was sprinkled into the main vessel and mixed until no fish eyes were present. The main vessel was then heated until 75-80° C. The components of Phase C were combined in a separate vessel and homogenized until a solution was obtained. The components of Phase C were heated to 75-80° C., if necessary, to dissolve the dutasteride. The components of Phase D were added to Phase C while heating to 75-80° C. and mixed until Phase D was completely melted. Phases C+D were added to the main manufacturing vessel at 75-80° C. with homogenization until the oil phase was fully incorporated. Phase E was used to rinse the Phase C+D vessel. The main manufacturing vessel as cooled to <30° C. Phase F was used to neutralize the batch to pH 5.5-6.0. Phase G was added to the main manufacturing vessel in an amount sufficient such that the total was 100% w/w.

Example 7: Topical Lotion Formulation Comprising Dutasteride (2019-045-76)

A topical formulation of 0.05% w/w for application may be prepared as follows.

| Phase | Ingredients | % w/w | IID Topical Max (% w/w) | Category |
|---|---|---|---|---|
| A | Sterile Water for Irrigation | 45.65 | 100.00 | Solvent |
|   | Sodium Hyaluronate | 0.10 | 2.50 | Humectant |
| B | Glycerin | 5.00 | 20.00 | Humectant Solvent |
|   | Xanthan Gum | 0.20 | 2.85 | Thickener |
| C | Methylparaben | 0.18 | 0.50 | Preservative |
| D | Diisopropyl Adipate | 20.00 | 20.00 | Solvent Emollient Penetration Enhancer |
|   | Dutasteride | 0.05 | — | API |
| E | Medium Chain Triglycerides | 15.00 | 20.00 | Solvent Emollient Penetration Enhancer |
|   | Isopropyl Palmitate | 7.30 | 7.30 | Solvent Emollient Penetration Enhancer |
| F | ARLACEL ® 165 | 3.00 | 7.50 | Nonionic Emulsifier |
|   | Sodium Monostearate | 0.50 | 8.00 | Nonionic Emulsifier |
|   | Cetearyl Alcohol | 3.00 | 12.00 | Thickener |
|   | Propylparaben | 0.02 | 5.25 | Preservative |
| G | Sterile Water for Irrigation | q.s. to 100 | 100.00 | Solvent |
|   | Total | 100.00 |   |   |

The components of Phase A were combined in the main manufacturing vessel with high agitation until a homogeneous gel was obtained. The components of Phase B were combined in a separate vessel. Phase B was added to the main manufacturing vessel and mixed until uniformly dispersed. Phase C was added to the main manufacturing vessel and mixed until dissolved. The main manufacturing vessel was then heated to 70-75° C. Phase D was combined in a separate vessel with homogenization until a solution was obtained. The phase was heated to 70-75° C. if necessary to dissolve the dutasteride. The components of Phase E were added to Phase D one at a time until a solution was obtained. The components of Phase F were added to Phases D+E while heating to 70-75° C. until Phase F was completely melted. Phases D+E+F were added to the main manufacturing vessel at 70-75° C. with homogenization until the oil phase was fully incorporated. Phase G was used to rinse the Phase D+E+F vessel. The main manufacturing vessel was cooled down to <30° C.

Example 8: Topical Lotion (Conditioner) Formulation Comprising Dutasteride (2019-045-63)

A topical formulation of 0.05% w/w for application may be prepared as follows.

| Phase | Ingredients | % w/w | IID Topical Max (% w/w) | Category |
|---|---|---|---|---|
| A | Sterile Water for Irrigation | 35.55 | 100.00 | Solvent |
|   | Stearalkonium Chloride | 0.50 | 4.20 | Cationic Emulsifier Conditioning Agent |
|   | Methylparaben | 0.18 | 0.50 | Preservative |
|   | Glycerin | 5.00 | 20.00 | Humectant Solvent |
| B | Olive Oil | 9.00 | 27.75 | Emollient |
|   | Benzyl Alcohol | 0.50 | 10.00 | Solvent Preservative Penetration Enhancer |
|   | Medium Chain Triglycerides | 15.00 | 20.00 | Solvent Emollient Penetration Enhancer |
|   | Diisopropyl Adipate | 20.00 | 20.00 | Solvent Emollient Penetration Enhancer |
|   | Dutasteride | 0.05 | — | API |
| C | PROMULGEN ® D | 5.00 | 8.00 | Emulsifier Thickener |
|   | Propylparaben | 0.02 | 5.25 | Preservative |
| D | Sterile Water for Irrigation | 1.00 | 100.00 | Solvent |
| E | Sterile Water for Irrigation | 8.00 | 100.00 | Solvent |
|   | Polyquaternium-10 | 0.20 | 2.06 | Conditioning Agent |
| F | Sterile Water for Irrigation | q.s. to 100 | 100.00 | Solvent |
|   | Total | 100.00 |   |   |

The components of Phase A were combined in the main manufacturing vessel and heated to 70-75° C., and mixed until uniform. The components of Phase B were combined in a separate vessel with homogenization until a solution was obtained. The components of Phase B were heated to 70-75° C., if necessary, to dissolve the dutasteride. The components of Phase C were added to Phase B while heating to 70-75° C., and mixed until Phase C was completely melted and incorporated. Phases B+C were added to the main manufacturing vessel at 70-75° C. with homogenization and mixed until the oil phase was fully incorporated. Phase D was used to rinse the Phase B+C vessel. The main manufacturing vessel was cooled to <40° C. The components of Phase E were combined in a separate vessel, then added to the main manufacturing vessel and mixed until uniform. The main manufacturing vessel was cooled to ≤30° C. Phase F was added to the batch in an amount sufficient such that the total was 100% w/w.

Example 9: Topical Lotion "Serum" Formulation Comprising Dutasteride (Dutasteride Dissolved in Oil Phase)

A topical formulation of 0.05% w/w for application may be prepared as follows.

| Phase | Ingredients | % w/w | IID Topical Max (% w/w) | Category |
|---|---|---|---|---|
| A | Sterile Water for Irrigation | q.s. to 100 (76.45) | 100.00 | Solvent |
|   | Glycerin | 5.00 | 20.00 | Humectant Solvent |
|   | Methylparaben | 0.18 | 0.50 | Preservative |
| B | CARBOPOL® 974P Polymer | 0.15 | 1.51 | Thickener |
| C | Medium Chain Triglycerides | 7.00 | 15.00 | Solvent Emollient Penetration Enhancer |
|   | Isopropyl Myristate | 3.00 | 50.30 | Solvent Emollient Penetration Enhancer |
|   | Diethyl Sebacate | 3.00 | 24.00 | Solvent Emollient |
|   | Propylparaben | 0.02 | 5.25 | Preservative |
| D | Dutasteride | 0.05 | — | API |
| E | PEMULEN® TR-1 | 0.15 | 0.80 | Thickener Emulsifier |
| F | 10% NaOH Solution | q.s. to pH 5.5-6.0 | pH adjuster | pH adjuster |
|   | Sterile Water for Irrigation | (5.00) | 100.00 | Solvent |
|   | Total | 100.00 | | |

The components of Phase A were combined in the main vessel and were mixed until a solution was obtained. The components of Phase B were sprinkled into the main vessel with vigorous mixing until no fish eyes were present. The components of Phase C were combined in a separate container and mixed until a solution was obtained. The component of Phase D was then added to Phase C and mixed until a solution was obtained. Phase E was then dispersed in combined Phases C+D. The combined Phases C+D+E were then added to the main vessel with vigorous propeller mixing for 20-30 minutes. The batch was then homogenized for 1 minute at 6,000 rpm. The pH of the batch was adjusted to pH 5.5-6.0 using the Phase F.

A topical lotion (serum) formulation of 0.05% w/w for application may be prepared as follows. (2019-045-25R)

| Phase | Ingredients | % w/w | IID Topical Max (% w/w) | Category |
|---|---|---|---|---|
| A | Sterile Water for Irrigation | q.s. to 100 (46.05) | 100.00 | Solvent |
|   | Glycerin | 5.00 | 20.00 | Humectant Solvent |
|   | Methylparaben | 0.18 | 0.50 | Preservative |
| B | CARBOPOL® 974P Polymer | 0.10 | 1.51 | Thickener |
| C | Oleyl Alcohol | 4.00 | 10.00 | Penetration Enhancer |
|   | Isopropyl Myristate | 20.45 | 50.30 | Solvent Emollient Penetration Enhancer |
|   | Diethyl Sebacate | 24.00 | 24.00 | Solvent Emollient Penetration Enhancer |
|   | Propylparaben | 0.02 | 5.25 | Preservative |
|   | Dutasteride | 0.05 | — | API |
| D | PEMULEN® TR-2 | 0.15 | 0.80 | Thickener Anionic Emulsifier |
| E | 10% NaOH Solution | q.s. to pH 5.5-6.0 | pH adjuster | pH adjuster |
|   | Sterile Water for Irrigation | | 100.00 | Solvent |
|   | Total | 100.00 | | |

The components of Phase A were combined in the main vessel and were mixed until a solution was obtained. The components of Phase B were sprinkled into the main vessel with vigorous mixing until no fish eyes were present. The components of Phase C were combined in a separate container and mixed until a solution was obtained. The component of Phase D was then added to Phase C and mixed until a solution was obtained. Phase E was then dispersed in combined Phases C+D. The combined Phases C+D+E were then added to the main vessel with vigorous propeller mixing for 20-30 minutes. The batch was then homogenized for 1 minute at 6,000 rpm. The pH of the batch was adjusted to pH 5.5-6.0 using the Phase F.

Example 10: Topical Gel Formulation Comprising Dutasteride

A topical formulation of 0.05% w/w for application may be prepared as follows. The light gel with a non-sticky finish can be applied on the scalp/hair and will advantageously not leave much residue after it sets.

| Phase | Ingredients | % w/w | IID Topical Max (% w/w) | Category |
|---|---|---|---|---|
| A | PEG 400 | q.s. to 100 (63.45) | 69.9 | Solvent |
|   | TRANSCUTOL® P | 15.00 | 49.91 | Solvent Penetration Enhancer |
|   | Diisopropyl Adipate | 20.00 | 20.00 | Solvent Emollient Penetration Enhancer |
| B | Dutasteride | 0.05 | — | API |
| C | KLUCEL® HG Pharm | 1.50 | 4.00 | Thickener |
|   | Total | 100.00 | | |

The components of Phase A were combined in the main vessel and were mixed until a solution was obtained. The components of Phase B were added to the main vessel and were mixed until a solution was obtained. Phase C was sprinkled into the main vessel and mixed until a uniform gel was obtained.

Example 11: Topical Gel Formulation Comprising Dutasteride

A topical formulation of 0.05% w/w for application may be prepared as follows. (2019-045-53)

| Phase | Ingredients | % w/w | IID Topical Max (% w/w) | Category |
|---|---|---|---|---|
| A | Dehydrated Alcohol | 47.92 | 96.94 | Solvent Penetration Enhancer |
|  | Propylene Glycol | 50.00 | 99.98 | Solvent Penetration Enhancer |
|  | Dutasteride | 0.05 | — | API |
| B | CARBOPOL ® 980 NF, Polymer | 2.03 | 1.40 | Thickener |
| C | Dehydrated Alcohol | q.s. to 100 | 96.94 | Solvent Penetration Enhancer |
|  | Total | 100.00 |  |  |

The components of Phase A were combined in the main manufacturing vessel until a solution was obtained. Phase B was slowly added to the main manufacturing vessel with mixing until a homogenous gel was obtained. Phase C was added to the main manufacturing vessel in an amount sufficient such that the total was 100% w/w.

A topical formulation of 0.05% w/w for application may be prepared as follows.

| Phase | Ingredients | % w/w | IID Topical Max (% w/w) | Category |
|---|---|---|---|---|
| A | Dehydrated Alcohol | q.s. to 100 (46.45) | 60.00 | Solvent Penetration Enhancer |
|  | Propylene Glycol | 50.00 | 99.98 | Solvent Penetration Enhancer |
|  | Dutasteride | 0.05 | — | API |
| B | CARBOPOL ® 980 NF, Polymer | 3.50 | 3.50 | Thickener |
|  | Total | 100.00 |  |  |

The components of Phase A were combined in the main manufacturing vessel until a solution was obtained. Phase B was slowly added to the main manufacturing vessel with mixing until a homogenous gel was obtained.

Example 12: Topical Gel Formulation Comprising Dutasteride

A topical formulation of 0.05% w/w for application may be prepared as follows. (2019-045-55)

| Phase | Ingredients | % w/w | IID Topical Max (% w/w) | Category |
|---|---|---|---|---|
| A | Propylene Glycol | q.s. to 100 (72.95) | 99.98 | Solvent Penetration Enhancer |
|  | TRANSCUTOL ® P | 20.00 | 49.91 | Solvent Penetration Enhancer |
|  | Diethyl Sebacate | 3.00 | 24.00 | Solvent Emollient Penetration Enhancer |
|  | Dutasteride | 0.05 | — | API |
| B | SEPINEO ® P 600 | 4.00 | 4.00 | Thickener Emulsifier |
|  | Total | 100.00 |  |  |

The components of Phase A were combined in the main manufacturing vessel until a solution was obtained. Phase B was added to the main manufacturing vessel with homogenization and mixed until a uniform gel was obtained.

Example 13: Topical Gel (Serum) Formulation Comprising Dutasteride

A topical formulation of 0.05% w/w for application may be prepared as follows. (2019-045-61)

| Phase | Ingredients | % w/w | IID Topical Max (% w/w) | Category |
|---|---|---|---|---|
| A | PEG 400 | q.s. to 100 (69.95) | 99.98 | Solvent |
|  | TRANSCUTOL ® P | 15.00 | 49.91 | Solvent Penetration Enhancer |
|  | Dutasteride | 0.05 | — | API |
| B | PEG 3350 | 15.00 | 40.00 | Viscosity Enhancer |
|  | Total | 100.00 |  |  |

The components of Phase A were combined in the main manufacturing vessel until a solution was obtained. Phase A was then heated to 60-65° C. Phase B was weighed out in a separate vessel and heated to 60-65° C. Phase B was then slowly added to the main manufacturing vessel and mixed until a homogenous gel was obtained and when the temperature was <30° C.

Example 14: Analysis of Binary Dutasteride/Excipient Compatibility Study

Samples were weighed out (about 500 mg to 100 mg of sample into a 40 mL VOA bottle). The samples were fully dispersed in 5.0 mL of hexane by vortex. Sonication was also used as needed to fully disperse the sample. 10 mL of diluent (water/acetonitrile 40/60) was added to the VOA bottle and mixed by Vortex. An aliquot was filtered through a 0.45 μm PTFE filter into an autosampler vial for HPLC analysis. For the standard, a 6-point calibration curve in the range of 10 μg/mL to 200 μg/mL of dutasteride in diluent was prepared.

The samples were analyzed via HPLC in accordance with the following parameters.

| Column | Water Symmetry C18, 3.5 µm, 3.0 × 150 mm |
|---|---|
| Mobile Phase A | Water/Acetonitrile/TFA (480/520/0.25) |
| Mobile Phase B | Acetonitrile |
| Injection Volume | 10 µl |
| Column Temperature | 35.0° C. |
| Sampler Temperature | Ambient |
| Flow Rate | 1.0 mL/min |
| Detection | Signal A: 220 nm |
| Run Time | 22.0 |

| Gradient | Time (min) | % Solvent B |
|---|---|---|
| | 0.0 | 0 |
| | 20.0 | 0 |
| | 21.0 | 95 |
| | 24.0 | 95 |
| | 24.1 | 0 |
| | 28.0 | 0 |

Various combinations of dutasteride and excipients were tested at T=0 and T=14 days after being stored at 50° C. to determine their stability and dutasteride's compatibility with different excipients. Results from the study are reported in FIG. 2.

Example 15: Treatment of Human Subjects Suffering from Alopecia with a Topical Composition of Dutasteride A topical composition of dutasteride, such as those described in Examples 1-13, can be applied to the scalp of a human subject suffering from alopecia for multiple days.

Two randomized, parallel-group studies can be conducted. Group I: 10 human subjects may receive 1 mL (1 mg) of the topical formulation of Example 1, applied to the scalp once a day (qd) or twice a day (b.i.d) for at least 4 weeks, alternatively at least 8 weeks, alternatively at least 12 weeks, alternatively at least 16 weeks.

Group 2 may receive a placebo without the dutasteride applied to the scalp once a day (qd) or twice a day (b.i.d) for at least 4 weeks, alternatively at least 8 weeks, alternatively at least 12 weeks, alternatively at least 16 weeks.

For each of the groups, hair thickness increase, target area hair count (TAHC), hair growth assessment (HGA), target area hair width (TAHW), scalp coverage, hair structure, and target area hair density (TAHD) can be measured every 2 weeks, alternatively every 4 weeks, alternatively every 8 weeks, alternatively every 12 weeks.

An increase in hair thickness, target area hair count (TAHC), target area hair width (TAHW), scalp coverage, hair structure, or target area hair density (TAHD) in Group 1 individual as compared to Group 2 individuals is indicative of a positive response to the topical treatment with dutasteride to alopecia.

Example 16: Treatment of Women Suffering from Hirsutism with a Topical Composition of Dutasteride Two randomized, parallel-group studies can be conducted. Group I: 10 women suffering from hirsutism can receive 1 mL (1 mg) of a topical formulation of dutasteride, such as those described in Examples 1-13, applied to the face once a day (q.d.) or twice a day (b.i.d) for at least 4 weeks, alternatively at least 8 weeks, alternatively at least 12 weeks, alternatively at least 16 weeks.

Group 2 may receive a placebo without the dutasteride applied to the face once a day (q.d.) or twice a day (b.i.d) for at least 4 weeks, alternatively at least 8 weeks, alternatively at least 12 weeks, alternatively at least 16 weeks.

For each of the groups, hair thickness decrease, target area hair count (TAHC), hair growth assessment (HGA), target area hair width (TAHW), hair structure, and target area hair density (TAHD) can be measured every 2 weeks, alternatively every 4 weeks, alternatively every 8 weeks, alternatively every 12 weeks.

A decrease in facial hair thickness, target area hair count (TAHC), facial hair width (TAHW), hair structure, and facial hair density (TAHD) of the women in Group 1 as compared to Group 2 is indicative of a positive response to the topical treatment with dutasteride to hirsuitism.

Example 17: Treatment of Men Suffering from Hypertrichosis with a Topical Composition of Dutasteride Two randomized, parallel-group studies can be conducted. Group I: 10 men suffering from hypertrichosis can receive 1 mL (1 mg) of a topical formulation of dutasteride, such as those described in Examples 1-13, applied to the face once a day (q.d.) or twice a day (b.i.d) for at least 4 weeks, alternatively at least 8 weeks, alternatively at least 12 weeks, alternatively at least 16 weeks.

Group 2 may receive a placebo without the dutasteride applied to the face once a day (q.d.) or twice a day (b.i.d) for at least 4 weeks, alternatively at least 8 weeks, alternatively at least 12 weeks, alternatively at least 16 weeks.

For each of the groups, hair thickness decrease, target area hair count (TAHC), hair growth assessment (HGA), target area hair width (TAHW), hair structure, and target area hair density (TAHD) can be measured every 2 weeks, alternatively every 4 weeks, alternatively every 8 weeks, alternatively every 12 weeks.

A decrease in facial hair thickness, target area hair count (TAHC), facial hair width (TAHW), hair structure, and facial hair density (TAHD) of the women in Group 1 as compared to Group 2 is indicative of a positive response to the topical treatment with dutasteride to hirsuitism.

Example 18: Treatment of Women Suffering from Hair Loss Secondary to Endocrine Therapy in Patients with Breast Cancer Two randomized, parallel-group studies can be conducted. Group I: 20 women suffering from hair loss secondary to endocrine therapy in patients with breast cancer can receive 0.5 mg of dutasteride in a topical formulation, such as those described in Examples 1-13, applied to the affected area of the scalp once a day (q.d.) or twice a day (b.i.d) for at least 4 weeks, alternatively at least 8 weeks, alternatively at least 12 weeks, alternatively at least 16 weeks.

Group 2 may receive a placebo without the dutasteride applied to the affected area of the scalp once a day (q.d.) or twice a day (b.i.d) for at least 1 week, alternatively up to 12 weeks.

For each of the groups, hair thickness increase, target area hair count (TAHC), hair growth assessment (HGA), target area hair width (TAHW), scalp coverage, hair structure, and target area hair density (TAHD) can be measured.

An increase in hair thickness, target area hair count (TAHC), target area hair width (TAHW), scalp coverage, hair structure, or target area hair density (TAHD) in Group 1 individual as compared to Group 2 individuals is indicative of a positive response to the topical treatment with dutasteride to alopecia.

Example 19: Treatment of Human Subjects Suffering from Alopecia with a Topical Composition of Dutasteride A patient suffering from alopecia may apply a dose of a topical formulation of dutasteride. The dutasteride topical formulation may be a solid formulation, such as a lotion, conditioner, serum, gel, foam, cream, paste, powder, oil, or gel. The dose may be 0.5 mg to 1.5 mg. The dutasteride topical formulation may be administered to the affected area once, hourly, b.i.d., t.i.d., q.i.d., or daily (q.d.) for 1 day, alternatively every 2 days, alternatively every 3 days, alternatively every 4 days, alternatively every 5 days, alternatively every 6 days, alternatively every week for at least 4 weeks, alternatively at least 8 weeks, alternatively at least 12 weeks, alternatively at least 16 weeks.

Example 20: Treatment of Women Suffering from Hirsutism with a Topical Composition of Dutasteride A patient suffering from hirsuitism may apply a dose of a topical formulation of dutasteride. The dutasteride topical formulation may be a solid formulation, such as a lotion, conditioner, serum, gel, foam, cream, paste, powder, oil, or gel. The dose may be 0.5 mg to 1.5 mg. The dutasteride topical formulation may be administered to the affected area once, hourly, b.i.d., t.i.d., q.i.d., or daily (q.d.) for 1 day, alternatively every 2 days, alternatively every 3 days, alternatively every 4 days, alternatively every 5 days, alternatively every 6 days, alternatively every week for at least 4 weeks, alternatively at least 8 weeks, alternatively at least 12 weeks, alternatively at least 16 weeks.

Example 21: Treatment of Men Suffering from Hypertrichosis with a Topical Composition of Dutasteride A patient suffering from hypertrichosis may apply a dose of a topical formulation of dutasteride. The dutasteride topical formulation may be a solid formulation, such as a lotion, conditioner, serum, gel, foam, cream, paste, powder, oil, or gel. The dose may be 0.5 mg to 1.5 mg. The dutasteride topical formulation may be administered to the affected area once, hourly, b.i.d., t.i.d., q.i.d., or daily (q.d.) for 1 day, alternatively every 2 days, alternatively every 3 days, alternatively every 4 days, alternatively every 5 days, alternatively every 6 days, alternatively every week for at least 4 weeks, alternatively at least 8 weeks, alternatively at least 12 weeks, alternatively at least 16 weeks.

Example 22: Treatment of Women Suffering from Hair Loss Secondary to Endocrine Therapy in Patients with Breast Cancer A patient suffering from breast cancer and hair loss secondary to endocrine therapy may apply a dose of a topical formulation of dutasteride. The dutasteride topical formulation may be a solid formulation, such as a lotion, conditioner, serum, gel, foam, cream, paste, powder, oil, or gel. The dose may be 0.5 mg to 1.5 mg. The dutasteride topical formulation may be administered to the affected area once, hourly, b.i.d., t.i.d., q.i.d., or daily (q.d.) for 1 day, alternatively every 2 days, alternatively every 3 days, alternatively every 4 days, alternatively every 5 days, alternatively every 6 days, alternatively every week for at least 4 weeks, alternatively at least 8 weeks, alternatively at least 12 weeks, alternatively at least 16 weeks.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

Which is claimed is:

1. A method for stimulating hair growth on a scalp of a human subject suffering from endocrine therapy-induced alopecia (ETIA), comprising:
   a) providing a topical composition comprising a therapeutically effective amount of dutasteride dissolved in a topical pharmaceutically acceptable excipient or carrier, wherein the topical composition is an emulsion comprising diethyl sebacate and oleyl alcohol and does not contain ethyl alcohol; and
   b) topically applying the composition to the scalp in an amount and for a duration sufficient to stimulate hair growth;
   wherein hair growth comprises an increase in scalp hair density, hair thickness, or scalp coverage.

2. The method of claim 1, wherein the ETIA is hair loss secondary to endocrine therapy for breast cancer.

3. The method of claim 1, wherein the composition is applied to the scalp in an area comprising the frontal, central, vertex regions, or a combination thereof of the scalp.

4. The method of claim 1, wherein the therapeutically effective amount of dutasteride is about 0.001% to about 1% (w/w).

5. The method of claim 4, wherein the therapeutically effective amount of dutasteride is about 0.075% (w/w).

6. The method of claim 1, wherein the composition does not contain polypropylene glycol.

7. The method of claim 1, wherein the composition further comprises a solvent selected from the group consisting of sterile water, glycerin, medium chain triglycerides, isopropyl myristate, diisopropyl adipate, isopropyl palmitate, propylene glycol, olive oil, castor oil, coconut oil, light mineral oil, diethylene glycol monoethylether, benzyl alcohol, cyclomethicone, PEG 400, dehydrated alcohol, and dimethyl isosorbide.

8. The method of claim 1, wherein the composition further comprises an emulsifier selected from the group consisting of stearalkonium chloride, sodium monostearate Laureth-4, Polysorbate 20, and PEG-35 Castor Oil.

9. The method of claim 1, wherein the dutasteride is dissolved in an oil phase of the emulsion.

10. The method of claim 1, wherein the composition further comprises a humectant, a thickener, a preservative, an emollient, an emulsifier, a pH adjuster, a penetration enhancer, and a conditioning agent.

11. The method of claim 1, wherein the therapeutically effective amount of dutasteride is about 0.002% to about 0.1% (w/w).

12. The method of claim 1, wherein the therapeutically effective amount of dutasteride is about 0.025% (w/w).

13. The method of claim 1, wherein the therapeutically effective amount of dutasteride is about 0.05% (w/w).

14. The method of claim 1, wherein the therapeutically effective amount of dutasteride is about 0.15% (w/w).

* * * * *